United States Patent
Miller, III

(10) Patent No.: US 8,472,654 B2
(45) Date of Patent: Jun. 25, 2013

(54) OBSERVER-BASED CANCELLATION SYSTEM FOR IMPLANTABLE HEARING INSTRUMENTS

(75) Inventor: Scott Allan Miller, III, Lafayette, CO (US)

(73) Assignee: Cochlear Limited, Macquarie University (AU)

( * ) Notice: Subject to any disclaimer, the term of this patent is extended or adjusted under 35 U.S.C. 154(b) by 1274 days.

(21) Appl. No.: 11/928,850

(22) Filed: Oct. 30, 2007

(65) Prior Publication Data

US 2009/0112051 A1   Apr. 30, 2009

(51) Int. Cl.
    *H04R 25/00* (2006.01)
(52) U.S. Cl.
    USPC ............ 381/312; 600/25; 607/57; 607/59
(58) Field of Classification Search
    USPC ............ 381/312; 600/25; 607/57, 59
    See application file for complete search history.

(56) References Cited

U.S. PATENT DOCUMENTS

| | | |
|---|---|---|
| 4,443,666 A | 4/1984 | Cote |
| 4,450,930 A | 5/1984 | Killion |
| 4,504,703 A | 3/1985 | Schneiter et al. |
| 4,532,930 A | 8/1985 | Crosby et al. |
| 4,606,329 A | 8/1986 | Hough |
| 4,607,383 A | 8/1986 | Ingalls |
| 4,621,171 A | 11/1986 | Wada et al. |
| 4,774,933 A | 10/1988 | Hough et al. |
| 4,815,560 A | 3/1989 | Madaffari |
| 4,837,833 A | 6/1989 | Madaffari |
| RE33,170 E | 2/1990 | Byers |
| 4,932,405 A | 6/1990 | Peeters et al. |
| 4,936,305 A | 6/1990 | Ashtiani et al. |
| 5,001,763 A | 3/1991 | Moseley |
| 5,015,224 A | 5/1991 | Maniglia |
| 5,105,811 A | 4/1992 | Kuzma |
| 5,163,957 A | 11/1992 | Sade et al. |
| 5,176,620 A | 1/1993 | Gilman |
| 5,277,694 A | 1/1994 | Leysieffer et al. |
| 5,363,452 A | 11/1994 | Anderson |
| 5,402,496 A | 3/1995 | Soli |
| 5,411,467 A | 5/1995 | Hortmann et al. |
| 5,456,654 A | 10/1995 | Ball |
| 5,475,759 A | 12/1995 | Engelbretson |
| 5,500,902 A | 3/1996 | Stockham, Jr. et al. |
| 5,554,096 A | 9/1996 | Ball |
| 5,558,618 A | 9/1996 | Maniglia |
| 5,624,376 A | 4/1997 | Ball et al. |
| 5,680,467 A | 10/1997 | Hansen |

(Continued)

FOREIGN PATENT DOCUMENTS

KR   20050117850 A   12/2005

*Primary Examiner* — Jerome Jackson, Jr.
*Assistant Examiner* — Dale E Page
(74) *Attorney, Agent, or Firm* — Lowe Hauptman Ham & Berner, LLP

(57) ABSTRACT

Provided is an implanted hearing instrument having reduced sensitivity to vibration. In this regard, the instrument differentiates between the desirable and undesirable signals within an implanted microphone response. In one arrangement, an observer identifies a current operating state of the implanted hearing instrument and one or more cancellation filters are adjusted based on the current operating state. The cancellation filter(s) are used to reduce undesired signals form the implanted microphone response. In a first arrangement, the output of the implanted hearing instrument may be filtered and removed from the implanted microphone response to reduce or substantially eliminate feedback in the microphone signal provided to an implanted signal processor.

22 Claims, 11 Drawing Sheets

U.S. PATENT DOCUMENTS

| | | | |
|---|---|---|---|
| 5,702,431 | A | 12/1997 | Wang et al. |
| 5,749,912 | A | 5/1998 | Zhang et al. |
| 5,754,662 | A | 5/1998 | Jolly et al. |
| 5,762,583 | A | 6/1998 | Adams et al. |
| 5,795,287 | A | 8/1998 | Ball et al. |
| 5,800,336 | A | 9/1998 | Ball et al. |
| 5,814,095 | A | 9/1998 | Muller et al. |
| 5,842,967 | A | 12/1998 | Kroll |
| 5,848,171 | A | 12/1998 | Stockham, Jr. et al. |
| 5,857,958 | A | 1/1999 | Ball et al. |
| 5,859,916 | A | 1/1999 | Ball et al. |
| 5,881,158 | A | 3/1999 | Lesinski et al. |
| 5,888,187 | A | 3/1999 | Jaeger et al. |
| 5,897,486 | A | 4/1999 | Ball et al. |
| 5,906,635 | A | 5/1999 | Maniglia |
| 5,912,977 | A | 6/1999 | Gottschalk-Schoenig |
| 5,913,815 | A | 6/1999 | Ball et al. |
| 5,951,601 | A | 9/1999 | Lesinski et al. |
| 6,031,922 | A | 2/2000 | Tibbetts |
| 6,044,162 | A | 3/2000 | Mead et al. |
| 6,072,884 | A | 6/2000 | Kates |
| 6,072,885 | A | 6/2000 | Stockham, Jr. et al. |
| 6,097,823 | A | 8/2000 | Kuo |
| 6,104,822 | A | 8/2000 | Melanson et al. |
| 6,108,431 | A | 8/2000 | Bachler |
| 6,128,392 | A | 10/2000 | Leysieffer et al. |
| 6,134,329 | A | 10/2000 | Gao et al. |
| 6,151,400 | A | 11/2000 | Seligman |
| 6,163,287 | A | 12/2000 | Huang |
| 6,173,063 | B1 | 1/2001 | Melanson |
| 6,198,971 | B1 | 3/2001 | Leysieffer |
| 6,330,339 | B1 | 12/2001 | Ishige et al. |
| 6,381,336 | B1 | 4/2002 | Lesinski et al. |
| 6,422,991 | B1 | 7/2002 | Jaeger |
| 6,626,822 | B1 | 9/2003 | Jaeger |
| 6,688,169 | B2 | 2/2004 | Choe et al. |
| 6,707,920 | B2 | 3/2004 | Miller |
| 6,736,771 | B2 | 5/2004 | Sokolich et al. |
| 6,807,445 | B2 | 10/2004 | Baumann |
| 7,214,179 | B2 | 5/2007 | Miller, III et al. |
| 2005/0222487 | A1* | 10/2005 | Miller et al. ............ 600/25 |
| 2006/0155346 | A1 | 7/2006 | Miller, III |
| 2007/0154030 | A1 | 7/2007 | Moses |

* cited by examiner

OBSERVER-BASED CANCELLATION SYSTEM FOR IMPLANTABLE HEARING INSTRUMENTS

FIELD

The present invention relates to implanted hearing instruments, and more particularly, to the cancellation of undesired signals from an output of an implanted microphone.

BACKGROUND

In the class of hearing aid systems generally referred to as implantable hearing instruments, some or all of various hearing augmentation componentry is positioned subcutaneously on, within, or proximate to a patient's skull, typically at locations proximate the mastoid process. In this regard, implantable hearing instruments may be generally divided into two sub-classes, namely semi-implantable and fully implantable. In a semi-implantable hearing instrument, one or more components such as a microphone, signal processor, and transmitter may be externally located to receive, process, and inductively transmit an audio signal to implanted components such as a transducer. In a fully implantable hearing instrument, typically all of the components, e.g., the microphone, signal processor, and transducer, are located subcutaneously. In either arrangement, an implantable transducer is utilized to stimulate a component of the patient's auditory system (e.g., ossicles and/or the cochlea).

By way of example, one type of implantable transducer includes an electromechanical transducer having a magnetic coil that drives a vibratory actuator. The actuator is positioned to interface with and stimulate the ossicular chain of the patient via physical engagement. (See e.g., U.S. Pat. No. 5,702,342). In this regard, one or more bones of the ossicular chain are made to mechanically vibrate, which causes the ossicular chain to stimulate the cochlea through its natural input, the so-called oval window.

As may be appreciated, a hearing instrument that proposes to utilize an implanted microphone will require that the microphone be positioned at a location that facilitates the receipt of acoustic signals. For such purposes, an implantable microphone may be positioned (e.g., in a surgical procedure) between a patient's skull and skin, for example, at a location rearward and upward of a patient's ear (e.g., in the mastoid region).

For a wearer of a hearing instrument including an implanted microphone (e.g., middle ear transducer or cochlear implant stimulation systems), the skin and tissue covering the microphone diaphragm may increase the vibration sensitivity of the instrument to the point where body sounds (e.g., chewing) and the wearer's own voice, conveyed via bone conduction, may saturate internal amplifier stages and thus lead to distortion. Also, in systems employing a middle ear stimulation transducer, the system may produce feedback by picking up and amplifying vibration caused by the stimulation transducer.

Certain proposed methods intended to mitigate vibration sensitivity may potentially also have an undesired effect on sensitivity to airborne sound as conducted through the skin. It is therefore desirable to have a means of reducing system response to vibration/noise (e.g., caused by biological sources and/or feedback), without affecting sound sensitivity. It is also desired not to introduce excessive electronic noise during the process of reducing the system response to vibration. These are the goals of the present invention.

SUMMARY

In an implantable hearing instrument utilizing an implanted microphone, it is often necessary to differentiate between desirable signals and undesirable signals. Desirable signals are those caused by outside or ambient sound, which causes tissue overlying an implanted microphone diaphragm to move relative to an inertial (non accelerating) microphone implant housing. This movement displaces an implanted microphone diaphragm. Accordingly, the implanted microphone generates an output that is indicative of the ambient sound. Undesirable signals may be those caused by vibration-noise. In this regard, undesired signals may be caused by relative movement between overlying tissue and an implanted implant housing which may result from the movement (e.g., due to acceleration, vibration, noise, etc.) of overlying tissue exerting a force on the implanted microphone diaphragm.

Differentiation between the desirable and undesirable signals may be at least partially achieved by utilizing one or more one-motion sensors to produce a motion signal(s) when an implanted microphone is in motion. Such a sensor may be, without limitation, an acceleration sensor and/or a velocity sensor. In any case, the motion signal is indicative of relative movement of the implanted microphone diaphragm and overlying tissue due to non-ambient sound sources such as motion/acceleration. In turn, this motion signal may be used to yield a microphone output signal that is less vibration sensitive.

That is, the output of the motion sensor (i.e., motion signal) may be processed with an output of the implantable microphone (i.e., microphone signal) to provide an audio signal that is less sensitive to non-ambient sources of vibration/noise than the microphone signal alone. For example, the motion signal may be appropriately scaled, phase shifted and/or frequency-shaped to match a difference in frequency response between the motion signal and the microphone signal. That is, a transfer function is determined between the motion sensor and the microphone. The motion signal may be processed according to the transfer function and the resulting processed signal may then be removed from the microphone signal to yield a net, improved audio signal employable for driving a middle ear transducer, an inner ear transducer and/or a cochlear implant stimulation system.

Stated otherwise, the motion sensor signal is shaped to estimate the microphone signal for common stimuli (e.g., acceleration, vibration). When the processed signal is combined with the microphone signal, this cancels the undesired signals in the microphone signal caused by the common stimuli. However, this also introduces motion sensor (e.g., accelerometer) electrical noise into the system. Further the shaping (e.g., filtering) of the motion sensor signal may amplify the electrical noise of the motion sensor. Accordingly, it may be desirable to cancel undesirable signals from the microphone signal without introducing electrical noise into the system. In such an arrangement the signal delivered to the patient may have a better signal to noise ratios (i.e, SNR) especially in the key intelligence band of 1-4 kHz.

Such cancellation, without introduction of electrical noise, may be performed by using the digital output of the hearing instrument. That is, a digital output signal of an implantable hearing instrument may be utilized to remove undesired signals from a microphone output signal (e.g., input signal of the implantable hearing instrument). As with a motion signal, the output signal of the implantable hearing instrument may be appropriately scaled, phase shifted and/or frequency-shaped according to a transfer function between the output and the microphone signal. In this regard, the transfer function may model the feedback path from an implanted auditory stimulation device to the implanted microphone. Again, the output signal may be processed according to the transfer function and the processed signal may be removed from the microphone signal to yield a net, improved audio signal. In this case however, the signals are all digital so there is no introduction and/or amplification of electrical noise into the system.

In order to scale, frequency-shape and/or phase shift a motion or output signal, a variety of signal processing filtering methods may be utilized. For instance, a filter may be utilized to model the transfer function between the motion sensor and the microphone and/or the output signal and the microphone. Such filters may be operative to scale the magnitude and phase of the signals such that they are made to substantially match the microphone signal for common stimuli. Accordingly, by removing a 'filtered' signal from a microphone signal, the effects of, for example, feedback associated with motion caused by operation of an implanted auditory stimulation device may be substantially reduced. Further, in the case of the motion sensor signal, generating a filter operative to manipulate the motion signal to substantially match the microphone signal for feedback caused by operation of the implanted auditory stimulation device (e.g., in response to inserted signal), may also allow for manipulating such a motion signal generated in response to undesired signals such as biological noise. In any case, the combination of a filter for filtering a signal (e.g., the motion signal and/or output signal) and the subsequent removal of that filtered signal from the microphone signal can be termed a cancellation filter. Accordingly, the output of the cancellation filter may be an estimate of the microphone acoustic response (i.e., the output signal with undesired signals removed).

Use of such a cancellation filter works well provided that the modeled transfer function of the system remains fixed. However, it has been determined that the transfer function changes with changes in the operating environment of the implantable hearing device. For instance, changes in skin thickness and/or the tension of the skin overlying the implantable microphone result in changes to the transfer function of the modeled systems. Such changes in skin thickness and/or tension may be a function of posture, biological factors (i.e., hydration) and/or ambient environmental conditions (e.g., heat, altitude, etc.). For instance, posture of the user may have a direct influence on the thickness and/or tension of the tissue overlying an implantable microphone. In cases where the implantable microphone is implanted beneath the skin of a patient's skin, turning of the patient's head from side to side may increase or decrease the tension and/or change the thickness of the tissue overlying the microphone diaphragm. As a result it is preferable that a cancellation filter be adaptive in order to provide cancellation that changes with changes in the operating environment of the implantable hearing instrument.

Accordingly, provided herein are systems and methods (i.e., utilities) that allow for adjusting the transfer function of a filter that is utilized to filter the digital output of an implanted hearing system such that the resulting filtered signal may be cancelled from an implanted microphone output signal. In this regard, the disclosed utilities utilize an observer that is operative to quickly determine, for example, changes in the operating conditions/environment of an implanted hearing instrument and to generate an output indicative thereof. Such an observer may be a module that is operative to determine one or more intended states of the microphone/motion sensor system. This output may then be utilized by the utility to adjust the digital filter to account for the changed operating conditions. Further, as such utilities utilize the digital output of the hearing instrument to cancel signals from the microphone signal, additional electrical noise is not introduced into the system.

According to a first aspect, a utility is provided for use with an implantable hearing instrument having an implanted microphone. The utility includes identifying a current operating condition of an implantable hearing instrument utilizing an observer. Based on the current operating condition as determined by the observer, filter settings may be established for a cancellation filter. Once such settings are determined, the cancellation filter may be utilized to cancel signals from a microphone output signal of the implantable microphone. In one arrangement, this entails filtering the digital output of the hearing instrument to generate a filtered output and combining this filtered output the microphone output signal to generate a net signal. This net signal may then be utilized (e.g., input) into signal processing componentry of the implantable hearing instrument for use in generating a subsequent output signal.

As may be appreciated, the cancellation filter may include a transfer function as determined between the output signal of the hearing instrument and the output signal of the microphone. Further, it will be appreciated that multiple such transfer functions may be identified for multiple operating conditions. Accordingly, upon determining the current operating condition by the observer, the utility may select an appropriate transfer function and/or interpolate between one or more transfer functions. Stated otherwise, filter coefficients for the cancellation filter may be selected based on the current operating conditions.

Use of an observer to identify current operating conditions may include the use of an observer that is operative to directly measure a current operating condition. In this regard, the observer may form a sensor that is adapted to directly measure one or more operating conditions/environments associated with the implantable system. In another arrangement, the observer is adapted to deduce parameters representative of current operating conditions. That is, in some instances the current operating condition may not be directly observable. In this latter regard, the observer may utilize another cancellation filter that utilizes a motion sensor to cancel undesired signals from the output signal of an implanted microphone.

In such an arrangement, a motion sensor output may be filtered by an adaptive filter and the resulting filtered motion signal may be cancelled from the microphone output signal. The filter may be adaptive such that by varying the coefficients of the filter, the filtered signal may be altered and, hence, the net signal generated by combining the filtered motion sensor signal with the microphone output signal may likewise be altered. More particularly the filter coefficients may be altered until the energy of the net signal is reduced to a desired degree (e.g., minimized). At such a time, the cancellation may be deemed adequate for the current operating conditions. Accordingly, the settings of the filter that achieves a desired degree of cancellation (i.e., cancellation appropriate for current operating conditions) may be utilized to establish filter coefficients for the filter that filters the output signal of the implantable hearing instrument for cancellation from the microphone output signal.

Unlike cancellation systems that do not use a motion sensor, this approach of setting the filter coefficients of the digital cancellation loop (i.e. cancellation system that removes the filtered digital output from the microphone output signal) based at least in part on settings of the motion sensor filter is relatively insensitive to correlation, so it does not completely cancel out simple sounds (like sirens and beeps). If desired, some portion of the net signal resulting from cancelling the motion sensor signal from the microphone signal can be mixed with the microphone signal cancelled by the filtered digital output signal to give a more natural sound. Such combination may allow for removing some biological noise from the signal input into the implantable hearing system.

In one particular arrangement, the coefficients of the motion sensor filter are all related to a common variable(s), which may include vector variable(s) as well as scalar variable(s). Accordingly, upon reducing the residual energy of the first net signal to the desired degree, a value of the common variable associated with a given operating condition (e.g., posture) may be identified. Accordingly, this value may be utilized in the generation of, for example, filter coefficients or other settings for the digital filter.

In this regard, it has been determined that it may be desirable to generate a variable system model that is dependent upon the operating conditions/environment of the implantable hearing instrument. However, it will be appreciated that the operating environment of the implantable hearing system may not be directly observable by the system. That is, the operating environment may comprise common variables that require estimation. In this regard, the common variable(s) may be termed a latent variable. As will be appreciated, in statistics a latent variable is one which is not directly observable but that can be deduced from observations of the system. For instance, the implantable hearing system may not have the ability to directly measure the thickness and/or tension of the tissue overlying an implantable microphone. Likewise, ambient environmental conditions (e.g., temperature, altitude) may not be observable by the hearing system. Accordingly, it may be desirable to generate a filter that is operative to adapt to current operating conditions without having direct knowledge of those operating conditions. For instance, the filter may be operative to iteratively adjust until a transfer function appropriate for the current operating conditions is identified.

In one arrangement, a variable system model may be utilized that includes coefficients that are each dependent on a common variable that is related to the operating environment of the hearing instrument. Such a common variable may include significantly fewer coefficients (e.g., two coefficients) that the number of coefficients for the filters (e.g., 7-30 coefficients). Such a system may allow for more quickly adapting (e.g., minimizing) the transfer function than a system that independently adjusts a larger number of different coefficients to minimize a transfer function. In one arrangement, this common variable may be the latent variable that is estimated by the system model. In such an arrangement, the system model may be operative to iteratively identify a value associated with the latent variable. For instance, such iterative analysis may entail filtering the motion sensor output using a plurality of different coefficient sets that are generated based on different estimated values of the latent variable. Further, the resulting filtered motion sensor signal may be subtracted from the microphone signal to generate a plurality of cancelled microphone signals (e.g., net signals). Typically, the cancelled microphone signal having the lowest energy level (e.g., residual energy) may be identified as having the most complete cancellation.

Accordingly, such a system model may be quickly adjusted to identify an appropriate transfer function for current operating conditions as only a common variable (e.g., a short vector variable) need be adjusted as opposed to adjusting individual filter coefficients to minimize error of the filter. That is, such a system may allow for rapid convergence on a transfer function optimized for a current operating condition. Additionally, the system may generate an indication of the current operating condition of the hearing system. For instance, the value of a latent variable that generates the cancelled microphone output having the lowest energy level may indicate a current state/operating condition for the system. This current state may be utilized as an observer value for selecting filter coefficients for other filters within the system.

According to another aspect, the system and method (i.e., utility) are provided for use in removing undesired signals from a microphone output signal. The method includes filtering a motion sensor output signal using a first filter and combining the resulting filtered motion sensor signal with a microphone output signal. Such combination results in the generation of a first net signal. The method further includes adjusting the first filter to reduce a residual energy of the first net signal. That is, the method may include iteratively adjusting the first filter, filtering the motion signal and combining the filtered motion signal with the microphone output signal. Such steps may be repeated until the residual energy of the net signal is reduced to a desired degree. At such time, the settings of the first filter may be utilized to establish filter settings of a second filter.

Such a second filter may be utilized to filter an output drive signal of the implantable hearing instrument and combine the filtered output drive signal with the output signal to the implantable microphone in order to reduce undesired signals therefrom. In one arrangement, such filtering is utilized to remove a feedback response caused by the actuation of an implantable auditory stimulation device

DETAILED DESCRIPTION

Reference will now be made to the accompanying drawings, which at least assist in illustrating the various pertinent features of the present invention. In this regard, the following description of a hearing instrument is presented for purposes of illustration aid description. Furthermore, the description is not intended to limit the invention to the form disclosed herein. Consequently, variations and modifications commensurate with the following teachings, and skill and knowledge of the relevant art, are within the scope of the present invention. The embodiments described herein are further intended to explain the best modes known of practicing the invention and to enable others skilled in the art to utilize the invention in such, or other embodiments and with various modifications required by the particular application(s) or use(s) of the present invention.

Figure 1:
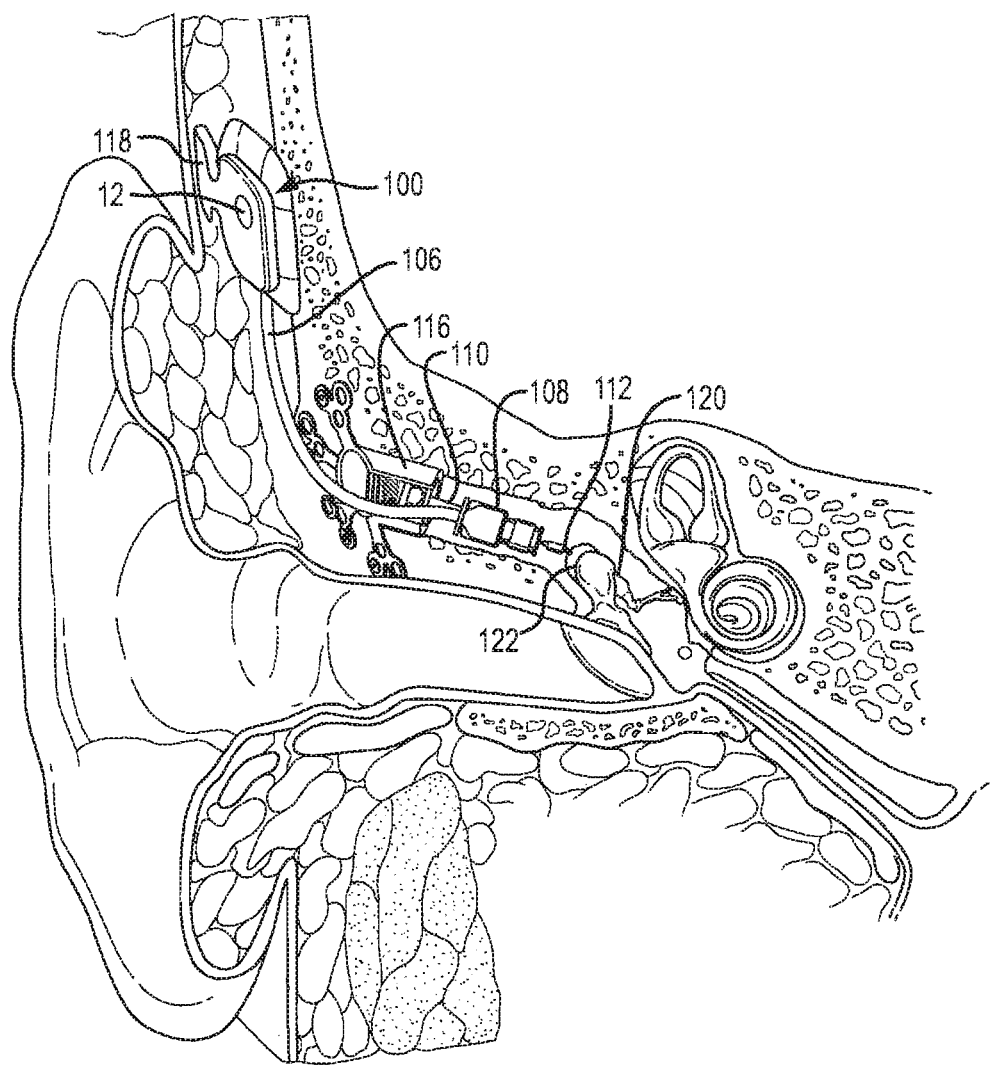
FIG. 1 illustrates a fully implantable hearing instrument as implanted in a wearer's skull.

FIG. 1 illustrates one application of the present invention. As illustrated, the application comprises a fully implantable hearing instrument system. As will be appreciated, certain aspects of the present invention may be employed in conjunction with semi-implantable hearing instruments as well as fully implantable hearing instruments, and therefore the illustrated application is for purposes of illustration and not limitation.

In the illustrated system, a biocompatible implant housing 100 is located subcutaneously on a patient's skull. The implant housing 100 includes a signal receiver 118 (e.g., comprising a coil element) and a microphone diaphragm 12 of an integrated microphone that is positioned to receive acoustic signals through overlying tissue. Though illustrated as utilizing an integrated microphone, it will be appreciated that an implanted microphone having a separate housing may be utilize das well. The implant housing 100 may further be utilized to house a number of components of the fully implantable hearing instrument. For instance, the implant housing 100 may house an energy storage device, a microphone transducer, and a signal processor. Various additional processing logic and/or circuitry components may also be included in the implant housing 100 as a matter of design choice. Typically, a signal processor within the implant housing 100 is electrically interconnected via wire 106 to a transducer 108.

The transducer 108 is supportably connected to a positioning system 110, which in turn, is connected to a bone anchor 116 mounted within the patient's mastoid process (e.g., via a hole drilled through the skull). The transducer 108 includes a connection apparatus 112 for connecting the transducer 108 to the ossicles 120 of the patient. In a connected state, the connection apparatus 112 provides a communication path for acoustic stimulation of the ossicles 120, e.g., through transmission of vibrations to the incus 122.

During normal operation, ambient acoustic signals (i.e., ambient sound) impinge on patient tissue and are received transcutaneously at the microphone diaphragm 12. Upon receipt of the transcutaneous signals, a signal processor within the implant housing 100 processes the signals to provide a processed audio drive signal via wire 106 to the transducer 108. As will be appreciated, the signal processor may utilize digital processing techniques to provide frequency shaping, amplification, compression, and other signal conditioning, including conditioning based on patient-specific fitting parameters. The audio drive signal causes the transducer 108 to transmit vibrations at acoustic frequencies to the connection apparatus 112 to effect the desired sound sensation via mechanical stimulation of the incus 122 of the patient.

Upon operation of the transducer 108, vibrations are applied to the incus 122, however, such vibrations are also applied to the bone anchor 116. The vibrations applied to the bone anchor are likewise conveyed to the skull of the patient from where they may be conducted to the implant housing 100 and, or to tissue overlying the microphone diaphragm 12. Accordingly such vibrations may be applied to the microphone diaphragm 12 and thereby included in the output response of the microphone. Stated otherwise, feedback from operation of the transducer 108 may be received by the implanted microphone diaphragm 12 via a feedback loop formed through tissue of the patient. Further, application of vibrations to the incus 122 may also vibrate the eardrum thereby causing sound pressure waves, which may pass through the ear canal where they may be received by the implanted microphone diaphragm 12 as ambient sound. Further, biological sources may also cause vibration (e.g., biological noise) to be conducted to the implanted microphone diaphragm 12 through the tissue of the patient. Such biological sources may include, without limitation, vibration caused by speaking, chewing, movement of patient tissue over the implant microphone (e.g. caused by the patient turning their head), and the like.

In any case, vibrations transmitted through the skull and/or tissue of the patient can cause undesired relative movement of the implant housing 100 and microphone diaphragm 12 to overlying tissue, or vice versa. Movement of the diaphragm 12 relative to the overlying tissue may result in the exertion of a force on the diaphragm 12. The exerted force may cause undesired vibration of the diaphragm 12 (i.e., non-ambient vibration), which may be included in the electrical output of the microphone as received sound. As noted above, two primary sources of undesired vibration are feedback from the implanted transducer 108 and biological noise. In either case, the vibration from these sources may cause undesired relative movement between overlying tissue and an implanted microphone diaphragm 12.

To actively address such sources of vibration and the resulting undesired relative movement between the diaphragm 12 and overlying tissue, the present embodiment utilizes the motion sensor 70 to provide an output response proportional to the vibrational movement experienced by an implanted microphone 10 and/or implant housing and, hence, the microphone diaphragm 12. See FIG. 2. Generally, the motion sensor 70 may be mounted anywhere within an implant housing and/or microphone 10 that allows the sensor 70 to provide an accurate representation of the non-ambient vibration received by the implanted microphone and diaphragm 12. In one arrangement, the microphone and motion sensor may be axially aligned to help match the response of these elements to common stimuli (e.g., acceleration and/or motion). In a further arrangement (not shown), the motion sensor may be a separate sensor that may be mounted to, for example, the skull of the patient. What is important is that the motion sensor 70 is at least partially isolated from the receipt of the ambient acoustic signals that pass transcutaneously through patient tissue and which are received by the microphone diaphragm 12. In this regard, the motion sensor 70 may provide an output response/signal that is indicative of undesired signals (e.g., caused by vibration and/or acceleration) whereas a transducer of the microphone 10 may generate an output response/signal that is indicative of both transcutaneously received acoustic/ambient sound signals from an ambient sound source 80 and undesired signals due to motion. Accordingly, the output response of the motion sensor may be removed from the output response of the microphone to reduce the effects of vibration/noise on the implanted hearing system.

Figure 2:
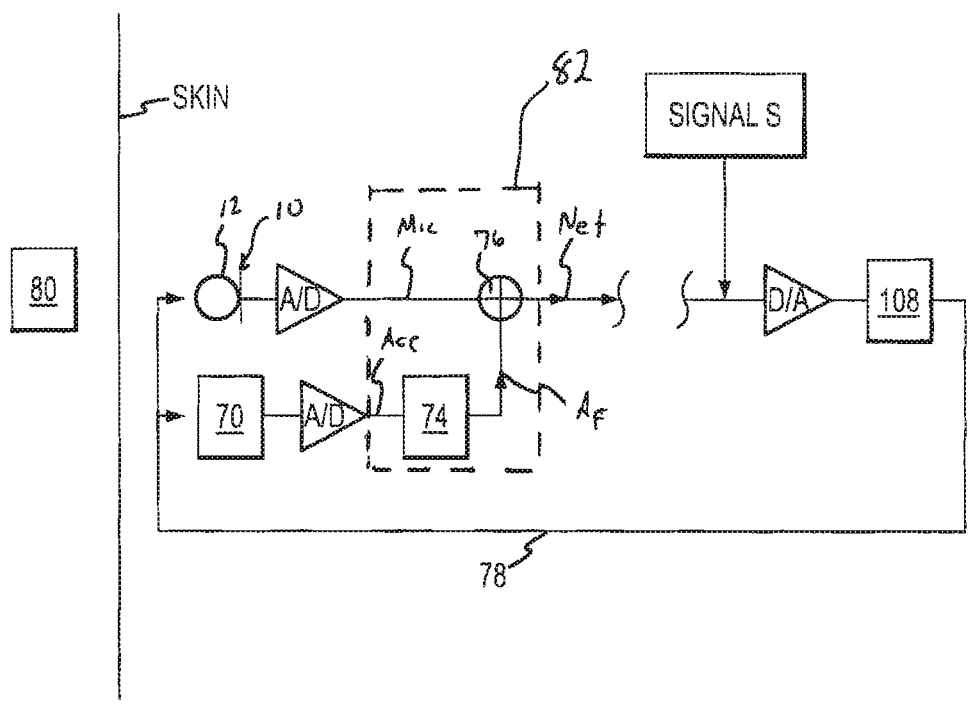
FIG. 2 is a schematic illustration of an implantable microphone system incorporating a motion sensor.

To remove undesired signals, including feedback and biological noise, the acceleration of the microphone 10 is measured using the motion sensor 70. As shown in FIG. 2, the motion sensor 70 further includes a filter 74, one embodiment of which may be implemented in an IIR filter, that is utilized for matching the output response Acc of the motion sensor 70 to the output response Mic of the microphone 10 prior to their combination (e.g., removal of Acc from Mic). Of note, the microphone 10 is subject to desired acoustic signals (i.e., from an ambient source 80), as well as undesired signals from biological sources (e.g., vibration caused by talking, chewing etc.) and feedback from the transducer 108 received by a tissue feedback loop 78. In contrast, the motion sensor 70 is at least partially isolated from the ambient acoustic source and is subjected more prominently to the undesired signals caused by the biological source and/or by feedback received via the feedback loop 78. Accordingly, the output of the motion sensor 70 corresponds to the undesired signal components of the microphone 10. However, the magnitude of the output channels (i.e., the output response Mic of the microphone 10 and output response Acc of the motion sensor 70) may be different and/or shifted in phase. In order to remove the undesired signal components from the microphone output response Mic, the filter 74 and/or the system processor may be operative to filter one or both of the responses to provide scaling, phase shifting and/or frequency shaping. The output response Mic of the microphone 10 and filtered motion sensor output response Af are then combined by summation unit 76, which generates a net output response Net that has a reduced response to the undesired signals. The combination of a filter 74 for filtering at least a motion sensor output response and a summation device 76 for combining a filtered motion sensor output response with a microphone output response defines a cancellation filter 82. It will be appreciated that the exact components of such a cancellation filter may vary. For instance, the filter may be static or adaptive. Further, each input channel (i.e., Mic or Acc) may include a filter.

In order to implement a filter 74 for scaling and/or phase shifting the output response Acc of a motion sensor 70 to remove the effects of feedback and/or biological noise from a microphone output response Mic, a system model of the relationship between the output responses of the microphone 10 and motion sensor 70 must be identified/developed. That is, the filter 74 must be operative to manipulate the output response Acc of the motion sensor 70 to biological noise and/or feedback, to replicate the output response Mic of the microphone 10 to the same biological noise and/or feedback. In this regard, the filtered output response Af and Mic may be of substantially the same magnitude and phase prior to combination (e.g., subtraction/cancellation). However, it will be noted that such a filter 74 need not manipulate the output response Acc of the motion sensor 70 to match the microphone output response Mic for all operating conditions. Rather, the filter 74 needs to match the output responses Acc and Mic over a predetermined set of operating conditions including, for example, a desired frequency range (e.g., an acoustic hearing range) and/or one or more pass bands. Note also that the filter 74 need only accommodate the ratio of microphone output response Mic to the motion sensor output response Acc to acceleration, and thus any changes of the feedback path which leave the ratio of the responses to acceleration unaltered have little or no impact on good cancellation. Such an arrangement thus has significantly reduced sensitivity to the posture, clenching of teeth, etc., of the patient.

Figure 3:
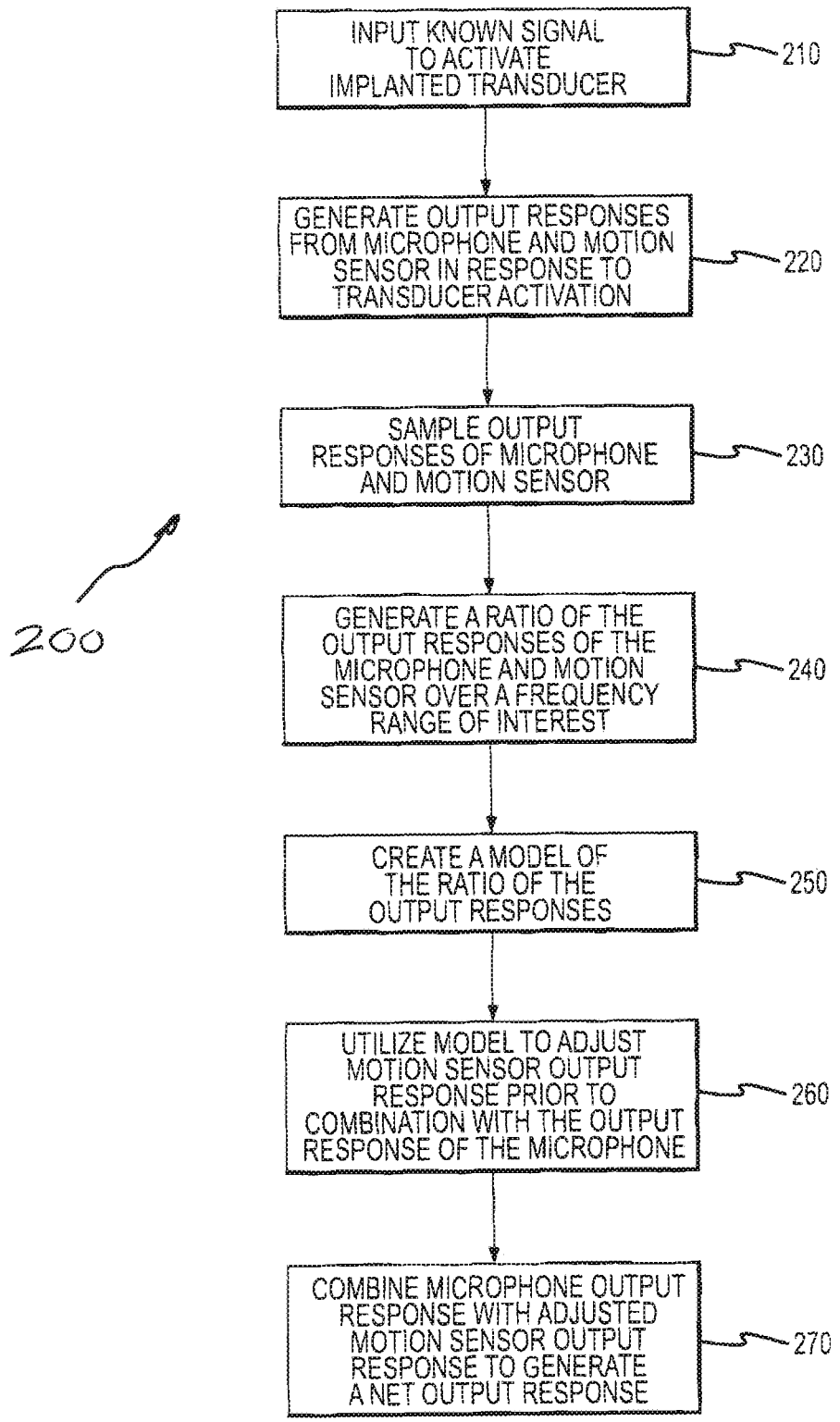
FIG. 3 is a process flow sheet.

Referring to FIG. 3, one method is provided for generating a system model that may be implemented as a digital filter for removing undesired signals from an output of an implanted microphone 10. However, it will be appreciated that other methods for modeling the system may be utilized and are within the scope of the present disclosure. As will be appreciated, a digital filter is effectively a mathematical manipulation of set of digital data to provide a desired output. Stated otherwise, the digital filter 74 may be utilized to mathematically manipulate the output response Acc of the motion sensor 70 to match the output response Mic of the microphone 10. FIG. 3 illustrates a general process 200 for use in generating a model to mathematically manipulate the output response Acc of the motion sensor 70 to replicate the output response Mic of the microphone 10 for a common stimulus. Specifically, in the illustrated embodiment, the common stimulus is feedback caused by the actuation of an implanted transducer 108. To better model the output responses Acc and Mic, it is generally desirable that little or no stimulus of the microphone 10 and/or motion sensor 70 occur from other sources (e.g., ambient or biological) during at least a portion of the modeling process.

Initially, a known signal S (e.g., a maximum length sequence/MLS signal) is input (210) into the system to activate the transducer 108. This may entail inputting (210) a digital signal to the implanted housing and digital to analog (D/A) converting the signal for actuating of the transducer 108. Such a drive signal may be stored within internal memory of the implantable hearing system, provided during a fitting procedure, or generated (e.g., algorithmically) internal to the implant during the measurement. Alternatively, the drive signal may be transcutaneously received by the hearing system. In any case, operation of the transducer 108 generates feedback that travels to the microphone 10 and motion sensor 70 through the feedback path 78. The microphone 10 and the motion sensor 70 generate (220) responses, Mic and Acc respectively, to the activation of the transducer 108. These responses (Acc and Mic) are sampled (230) by an A/D converter (or separate A/D converters). For instance, the actuator 108 may be actuated in response to the input signal(s) for a short time period (e.g., a quarter of a second) and the output responses may be each be sampled (230) multiple times during at least a portion of the operating period of the actuator. For example, the outputs may be sampled (230) at a 16000 Hz rate for one eighth of a second to generate approximately 2048 samples for each response Acc and Mic. In this regard, data is collected for the responses of the microphone (Mic) and accelerometer (Acc).

Figure 4:
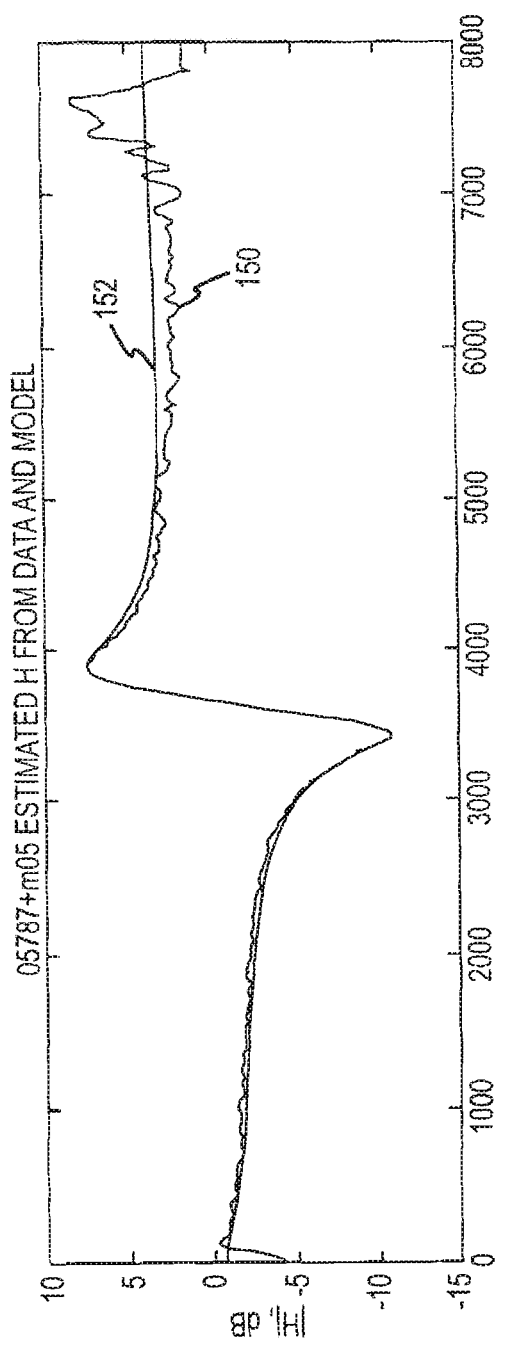
FIG. 4 is a plot of the ratios of the magnitudes of output responses of an implanted microphone and motion sensor.

In the present embodiment, frequency domain output responses of the microphone and accelerometer are utilized to create a mathematical model between the responses Acc and Mic. A plot of the ratio of the magnitudes of the microphone response to the accelerometer response over a frequency range of interest may then be generated (240). FIG. 4 illustrates the ratio of the output responses of the microphone 10 and motion sensor 70. As shown, the jagged magnitude ratio line 150 represents the ratio of the responses over a frequency range between zero and 8000 Hz. As may be appreciated, a variety of system identification techniques may be utilized to determine the desired filter coefficients. See for example "System Identification: Theory for the User", Lennart Ljung, Prentice Hall 1999. Such techniques may include, for example, time domain techniques and/or frequency domain techniques.

The plots of the ratios of the magnitudes of the microphone and motion sensor responses Mic and Acc may then be utilized to create (250) a mathematical model (whose implementation is the filter) for adjusting the output response Acc of the motion sensor 70 to match the output response Mic of the microphone 10. Stated otherwise, the ratio of the output responses provides a frequency response between the motion sensor 70 and microphone 10 and may be modeled create a digital filter. In this regard, the mathematical model may consist of a function fit to one or both plots. For instance, in FIG. 4, a function 152 may be fit to the magnitude ratio plot 150. The type and order of the function(s) may be selected in accordance with one or more design criteria. Complex frequency domain data, representing both magnitude and phase, may be used to assure good cancellation. Once the ratio(s) of the responses are modeled, the resulting mathematical model may be implemented as the digital filter 74. As will be appreciated, the frequency plots and modeling may be performed internally within the implanted hearing system, or, the sampled responses may be provided to an external processor (e.g., a PC) to perform the modeling.

Once a function is properly fitted to the ratio of responses, the resulting digital filter may then be utilized (260) to manipulate (e.g., scale and/or phase shift) the output response Acc of the motion sensor prior to its combination with the microphone output response Mic. The output response Mic of the microphone 10 and the filtered output response Af of the motion sensor may then be combined (270) to generate a net output response Net (e.g., a net audio signal).

A number of different digital filters may be utilized to model the ratio of the microphone and motion sensor output responses. Such filters may include, without limitation, LMS filters, max likelihood filters, adaptive filters and Kalman filters. Two commonly utilized digital filter types are finite impulse response (FIR) filters and infinite impulse response (IIR) filters. Each of the types of digital filters (FIR and IIR) possess certain differing characteristics. For instance, FIR filters are unconditionally stable. In contrast, IIR filters may be designed that are either stable or unstable. One method for generating such a filter is provided in co-pending U.S. patent application Ser. No. 11/330,788, entitled, "Active Vibration Attenuation for Implantable Microphone," having a filing date of Jan. 11, 2006, the entire contents of which are incorporated by reference herein.

By generating a filter that manipulates the motion sensor output response to substantially match the microphone output response for feedback caused by the operation of the transducer, the filter may also be operative to manipulate the motion sensor output response to biological noise substantially match the microphone output response to the same biological noise. That is, the filter is operative to least partially match the output responses for any common stimuli. Further, the resulting combination of the filter for filtering the motion sensor output response and the subsequent subtraction of the filtered motion sensor output response from the microphone output response represents a cancellation filter 82. The output of this cancellation filter 82 is a canceled signal that is an estimate of the microphone response to acoustic (e.g., desired) signals.

As discussed above, the filter is an algorithm (e.g., a higher order mathematical function) having static coefficients. That is, the resulting filter has a fixed set of coefficients that collectively define the transfer function of the filter. Such a filter works well provided that the transfer function remains fixed. However, in practice the transfer function changes with the operating environment of the implantable hearing instrument. For instance, changes in thickness and/or tension of skin overlying the implantable microphone change the operating environment of the implantable hearing instrument. Such changes in the operating environment may be due to changes in posture of the user, other biological factors, such as changes in fluid balance and/or ambient environment conditions, such as temperature, barometric pressure etc. A filter having static coefficients cannot adjust to changes in operating conditions/environment of the implantable hearing system. Accordingly, changes in the operating conditions/environment may result in feedback and/or noise being present in the canceled signal. Therefore, to provide improved cancellation, the filter may be made to be adaptive to account for changes in the operating environment of the implantable hearing instrument.

Figure 5:
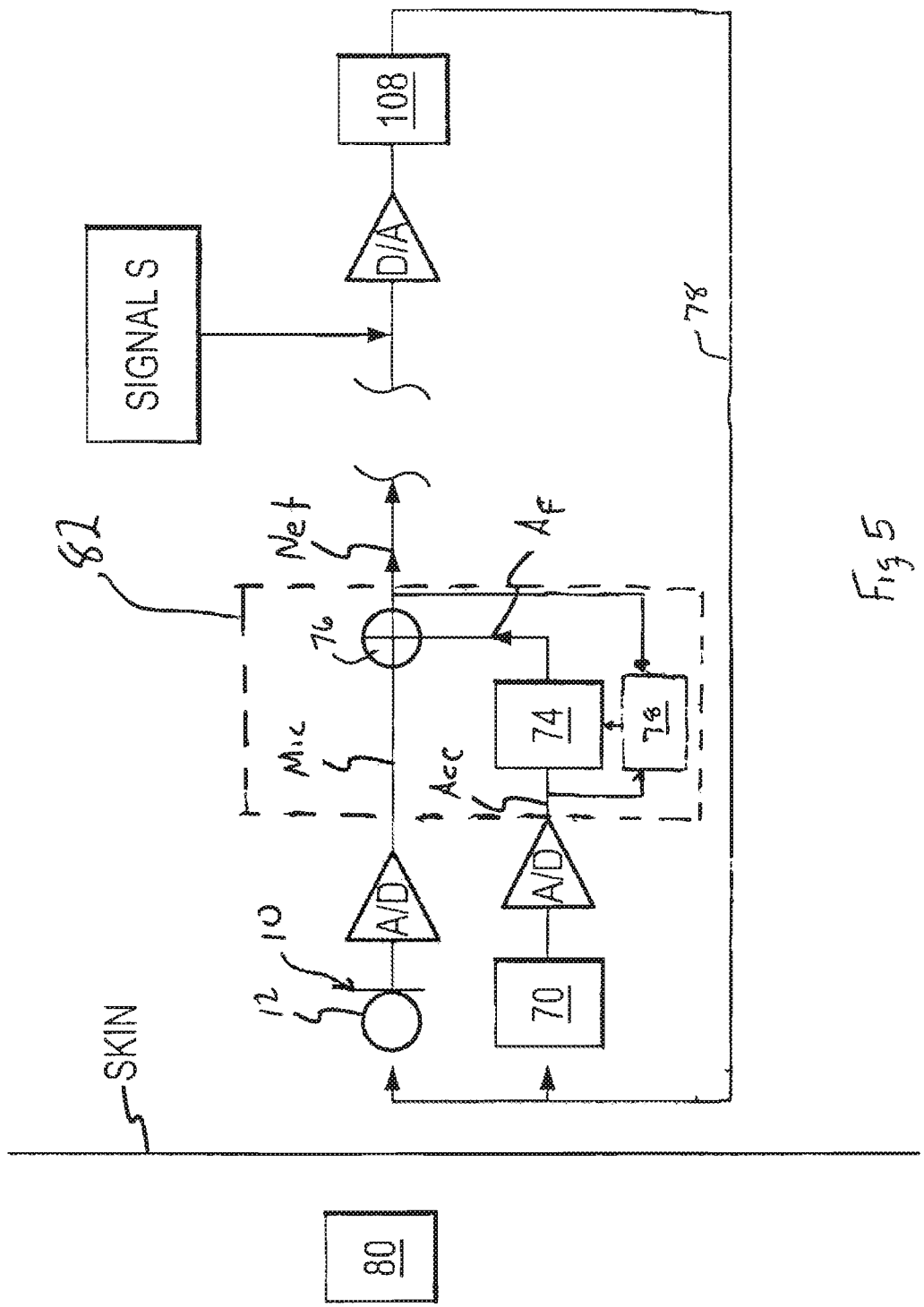
FIG. 5 is a schematic illustration of an implantable microphone system incorporating a motion sensor and an adaptive cancellation filter.

FIG. 5 illustrates one embodiment of a system that utilizes an adaptive filter 74a. In this embodiment, an adaptive algorithm 78 adjusts coefficients of the adaptive filter 74a to reduce (e.g., minimize) the residual energy in the net output (i.e., the combination of the microphone output response and filtered motion signal). Such an adaptive system may allow the cancellation filter to adapt to changes in the transfer function.

The adaptive algorithm 78 can perform this process using the output response of the motion sensor 70 and net output response. As known to those skilled in the art, the adaptive algorithm 78 and adjustable filter 74a can take on many forms, such as continuous, discrete, finite impulse response (FIR), infinite impulse response (IIR), lattice, systolic arrays, etc.,—see for example "Adaptive Filter Theory", Simon Haykin, Prentice Hall 1991 for a more complete list—all of which have be applied successfully to adaptive filters. Well-known algorithms for the adaptation algorithm include stochastic gradient-based algorithms such as the least-mean-squares (LMS) and recursive algorithms such as RLS. There are algorithms which are numerically more stable such as the QR decomposition with RLS (QRD-RLS), and fast implementations somewhat analogous to the FFT. The adaptive filter 74a may incorporate an observer, that is, a module to determine one or more intended states of the microphone/motion sensor system. The observer may use one or more observed state(s)/variable(s) to determine proper or needed filter coefficients. Converting the observations of the observer to filter coefficients may be performed by a function, look up table, etc. Adaptive algorithms especially suitable for application to lattice IIR filters may be found in, for instance, "Adaptive IIR Filtering in Signal Processing and Control", P. A. Regalia, Marcel Dekker 1995, Adaptation algorithms can be written to operate largely in the DSP "background," freeing needed resources for real-time signal processing.

As will be appreciated, adaptive filters are typically operative to adapt their performance based on the input signal to the filter. In tlis regard, the algorithm of an adaptive filter may be operative to use signal feedback (e.g., the net response) to refine values of its filter coefficients and thereby enhance its frequency response. Generally, in adaptive cancellation, the algorithm contains the goal of minimizing a "loss function" J. The loss function is typically designed in such a way as to minimize the impact of mismatch. One common loss function in adaptive filters is the least mean square error. This is defined as:

$$J(\theta) = \tfrac{1}{2} E(\tilde{y}_m(\theta)^2) \qquad \text{Eq. 1}$$

where $\tilde{y}_m$ is a cancelled output of the microphone which represents the microphone output minus a prediction of the microphone response to undesired signals; where E is the expected value, and $\theta$ is a vector of the parameters (e.g., tap weight of multiple coefficients) that can be varied to minimize the value of J. This is to say, the algorithm has the goal of minimizing the average of the cancelled output signal squared. Setting the derivative of J to zero finds the extreme, including the minimum, values:

$$\partial_\theta J = \tfrac{1}{2} E(\partial_\theta (\tilde{y}_m(\theta)^2)) = E(\tilde{y}_m(\theta) \partial_\theta \tilde{y}_m(\theta)) = 0 \qquad \text{Eq. 2}$$

If this equation is then solved for the vector $\theta$, J will be minimized, so that as much of the signal correlated with the motion sensor will be removed from the microphone output. One method for solving such an equation is provided in co-pending U.S. application Ser. No. 11/565,014, entitled, "Adaptive Cancellation System for Implantable Hearing Instruments," having a filing date of Nov. 30, 2006, the contents of which are incorporated by reference within.

Most adaptive filter algorithms work to remove any correlation between the output and the input. Removing any signal correlated with the motion sensor output is not desirable for all signals; a sinewave input will result in a sinewave output, which will be correlated with the input. As a result, one conventional NLMS FIR implementation may attempt to remove the sinewave component completely, so that a pure tone will be rapidly and completely removed from the output signal. Such is also true of feedback control using the implant output (e.g., drive signal) instead of the motion sensor output, provided the same type of algorithm is used. One demonstration of noise removal in adaptive filters demonstrated the rapid and complete removal of a warbling "ambulance" tone; removal of alarm tones, many of which are highly correlated, would be a drawback for any patient using such a device. Music is also highly self-correlated, so that music quality often suffers in conventional hearing aids at the hands of feedback control circuitry. Fortunately, the autocorrelation of speech has support only for very small values of lags, and thus is not well self-correlated, and is not usually greatly impacted by feedback cancellation systems in conventional hearing aids.

Accordingly, in some instances an IIR (infinite impulse response) filter may be a better choice for the adaptive filter model. Such an adaptive filter can compactly and efficiently compute with a few terms transfer functions that would take many times (sometimes hundreds) as many FIR terms. Unfortunately, it has traditionally been very difficult to implement adaptive IIR filters. The issues are primarily with stability and computation of the gradient. The traditional approaches to this problem are all computationally intensive or can produce unsatisfactory results.

IIR filters, unlike FIR filters, contain poles in their response and can become unstable with any combination of input parameters that result in a pole outside of the unit circle in z space. As a result, the stability of a set of coefficients must be determined before presentation to the filter. With a conventional "direct" form of IIR filter, it is computationally intensive to determine the stability. Other forms of IIR filter, such as the lattice filter, are easier to stabilize but require more computational steps. In the case of the lattice filter, there will be about 4 times as many arithmetic operations performed as with the direct form.

The gradient of IIR filters can also be difficult to compute. The most common approaches are to abandon the proper use of minimization entirely and adopt what is known as an equation error approach. Such an approach uses an FIR on both of the channels, and results in a simple, easy to program structure that does not minimize the residual energy. Another approach is to use an iterative structure to calculate the gradient. This approach is generally superior to using equation error, but it is computationally intensive, requiring about as much computation as the IIR filter itself.

A conventional adaptive IIR filter will normally do its best to remove any signal on the mic that is correlated with the motion sensor output response, including removing signals such as sinewaves, music and alarm tones. As a result, the quality of the signal may suffer, or the signal may be eliminated altogether. Finally, the IIR filter, like the FIR filter, can have slow convergence due to the range between its maximum and minimum values.

Figure 6:
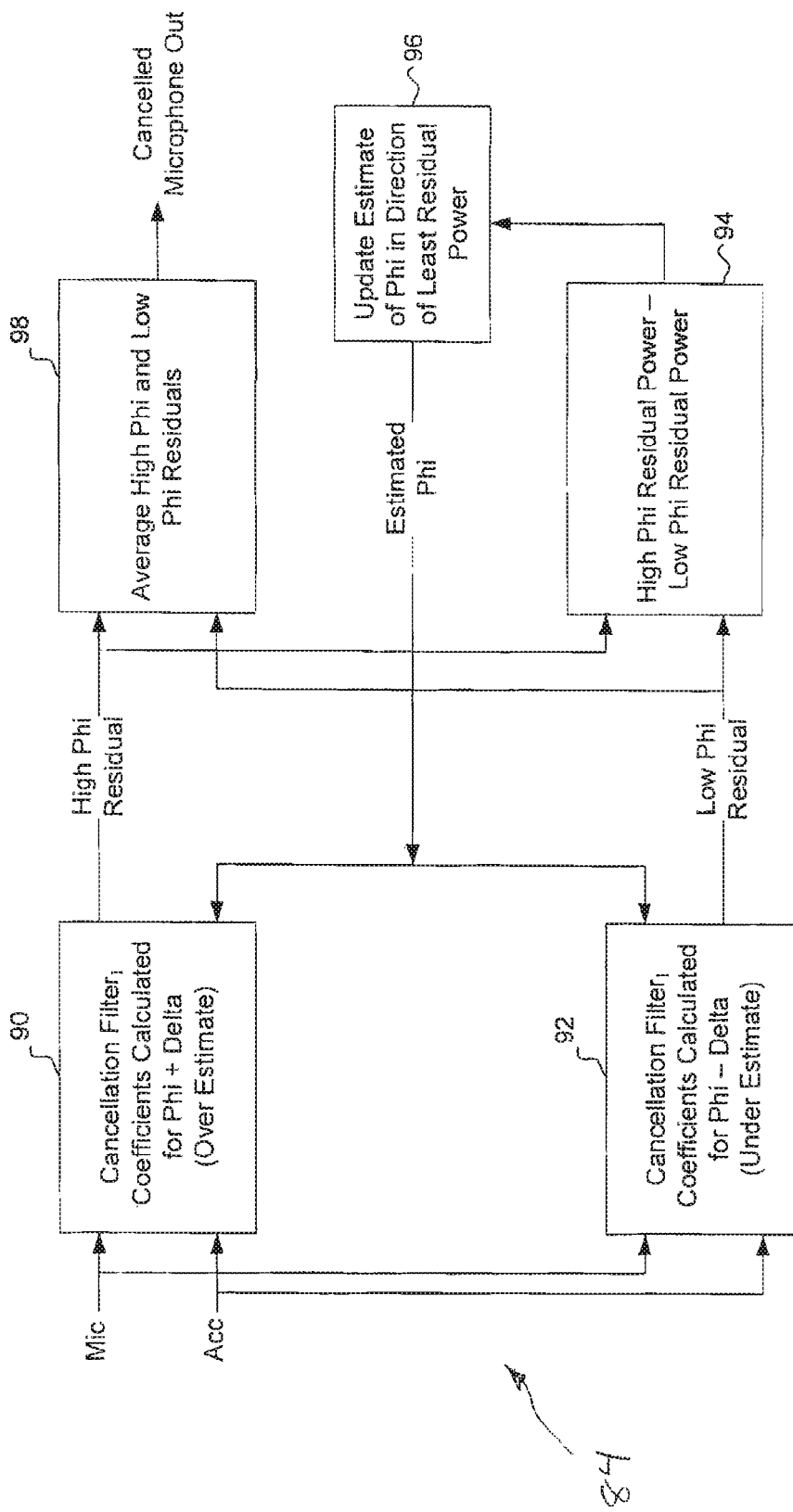
FIG. 6 is a schematic illustration of one embodiment of an implanted hearing system that utilizes first and second cancellation filters.

FIG. 6 provides a system that utilizes an adaptive filter arrangement that overcomes the drawbacks of some existing filters. In this regard, the system utilizes an adaptive filter that is computationally efficient, converges quickly, remains stable, and is not confused by correlated noise. To produce such an adaptive filter, the system of FIG. 6 utilizes an adaptive filter that adapts based on the current operating conditions (e.g., operating environment) of the implantable hearing instrument. However, it will be appreciated that such operating conditions are often not directly observable. That is, the operating conditions form latent parameters or variables. Accordingly, the system is operative to estimate the latent variable(s) for purposes of adapting to current operating conditions. Stated otherwise, the system utilizes a latent variable adaptive filter.

The latent variable adaptive filter (LVAF) is computationally efficient, converges quickly, can be easily stabilized, and its performance is robust in the presence of correlated noise. It is based on IIR filters, but rather than adapting all the coefficients independently, it uses the functional dependence of the coefficients on a latent variable, which may include a vector variables and/or scalar variables. In statistics, a latent variable is one which is not directly observable, but that can be deduced from observations of the system. An example of a latent variable is the thickness of the tissue over the microphone. This cannot be directly measured, but can be deduced from the change in the microphone motion sensor (i.e., mic/acc) transfer function.

Another hidden variable may be user "posture." It has been noted that some users of implantable hearing instruments experience difficulties with feedback when turning to the left or the right (usually one direction is worse) if the (nonadaptive) cancellation filter has been optimized with the patient facing forward. Posture could be supposed to have one value at one "extreme" position, and another value at a different "extreme" position. "Extreme," in this case, is flexible in meaning; it could mean at the extreme ranges of the posture, or it could mean a much more modest change in posture that still produces different amounts of feedback for the patient. Posture in this case may be a synthetic hidden variable (SHV), in that the actual value of the variable is arbitrary; what is important is that the value of the hidden variable changes with the different measurements. For instance, the value of the SHV for posture could be "+90" for the patient facing all the way to the right, and "−90" for a patient facing all the way to the left, regardless of whether the patient actually rotated a full 90 degrees from front. The actual range of the SHV is arbitrary, and could be "−1" and "−+1," or "0" and "+1" if such ranges lead to computational simplification.

In the case of posture, it is relatively easy to assign a physical parameters to the SHV, such as the angle that the patient is turned from facing forward. However, there are other cases in which the variable is truly hidden. An example might be where the patient activates muscle groups internally, which may or may not have any external expression. In this case, if the tonus and non-tonus conditions affect the feedback differently, the two extreme conditions could be given values of "0" and "+1," or some other arbitrary values. One of the advantage of using SHVs is that only the measurements of the vibration/motion response of the microphone assembly need to be made, there is no need to measure the actual bidden variable. That is, the hidden variable(s) can be estimated and/or deduced.

As shown in FIG. 6, an adaptive cancellation system 84 utilizes two adaptive cancellation filters 90 and 92 instead of one cancellation filter. The cancellation filters are identical and each cancellation filter 90, 92, includes an adaptive filter (not shown) for use in adjusting the motion output signal, Acc, to match the microphone output signal, Mic, and thereby generate a filtered motion signal. Additionally, each cancellation filter includes a summation device (not shown) for use in removing filtered motion signals from the microphone output signal and thereby generating first and second cancelled signals that are estimates of the microphone response to desired signals (e.g., ambient acoustic signals). Each adaptive cancellation filter 90, 92 estimates a latent variable 'phi', a vector variable which represents the one or more dimensions of posture or other variable operating conditions that changes in the patient, but whose value is not directly observable. The estimate of the latent variable phi is used to set the coefficients of the cancellation filters to cancel out undesired microphone signals (e.g., noise) caused by, for example, feedback and biological noise. In this regard, all coefficients of the filters 90, 92 are dependent upon the latent variable phi. After cancellation, one, both or a combination of the first and second cancelled microphone signals (e.g., essentially the acoustic signal) are passed onto the remainder of the hearing instrument signal processing.

In order to determine the value of the latent variable phi that provides the best cancellation, the coefficients of the first cancellation filter 90 are set to values based on an estimate of the latent variable phi. In contrast, the coefficients of the second cancellation filter 92, called the scout cancellation filter 92, are set to values based on the estimate of the latent viable phi plus (or minus) a predetermined value delta "δ." Alternatively, the coefficients of the first filter 90 may be set to values of the latent variable plus delta and the coefficients of the second filter may be set to values of the latent variable minus delta. In this regard, the coefficients of the second adaptive filter 92 are slightly different than the coefficients of the first filter 90. Accordingly, the energies of the first and second cancelled signals or residuals output by the first and second adaptive cancellation filters 90, 92 may be slightly different. The residuals, which are the uncancelled portion of the microphone signal out of each cancellation filter 90, 92, are compared in a comparison module 94, and the difference in the residuals are used by the Phi estimator 96 to update the estimate of phi (e.g., adjust up or down). Accordingly, the process may be repeated until the value of phi is iteratively determined. In this regard, phi may be updated until the residual value of the first and second cancellation filters is substantially equal. At such time, either of the cancelled signals may be utilized for subsequent processing, or, the cancelled signals may be averaged together in a summation device 98 and then processed.

Adjustment of the latent variable phi based on the comparison of the residuals of the cancelled signals allows for quickly adjusting the cancellation filters to the current operating conditions of the implantable hearing instrument. To further speed this process, it may be desirable to make large adjustments (i.e., steps) of the latent value, phi. For instance, if the range of the phi is known (e.g., 0 to 1) an initial mid range estimate of phi (e.g., ½) may be utilized as a first estimate. Likewise, the step size of the adjustment of phi may be relatively large (e.g., 0.05 or 0.1) to allow for quick convergence of the filter coefficients to adequately remove noise from the microphone output signal in response to changes in the operating conditions.

Figure 7:
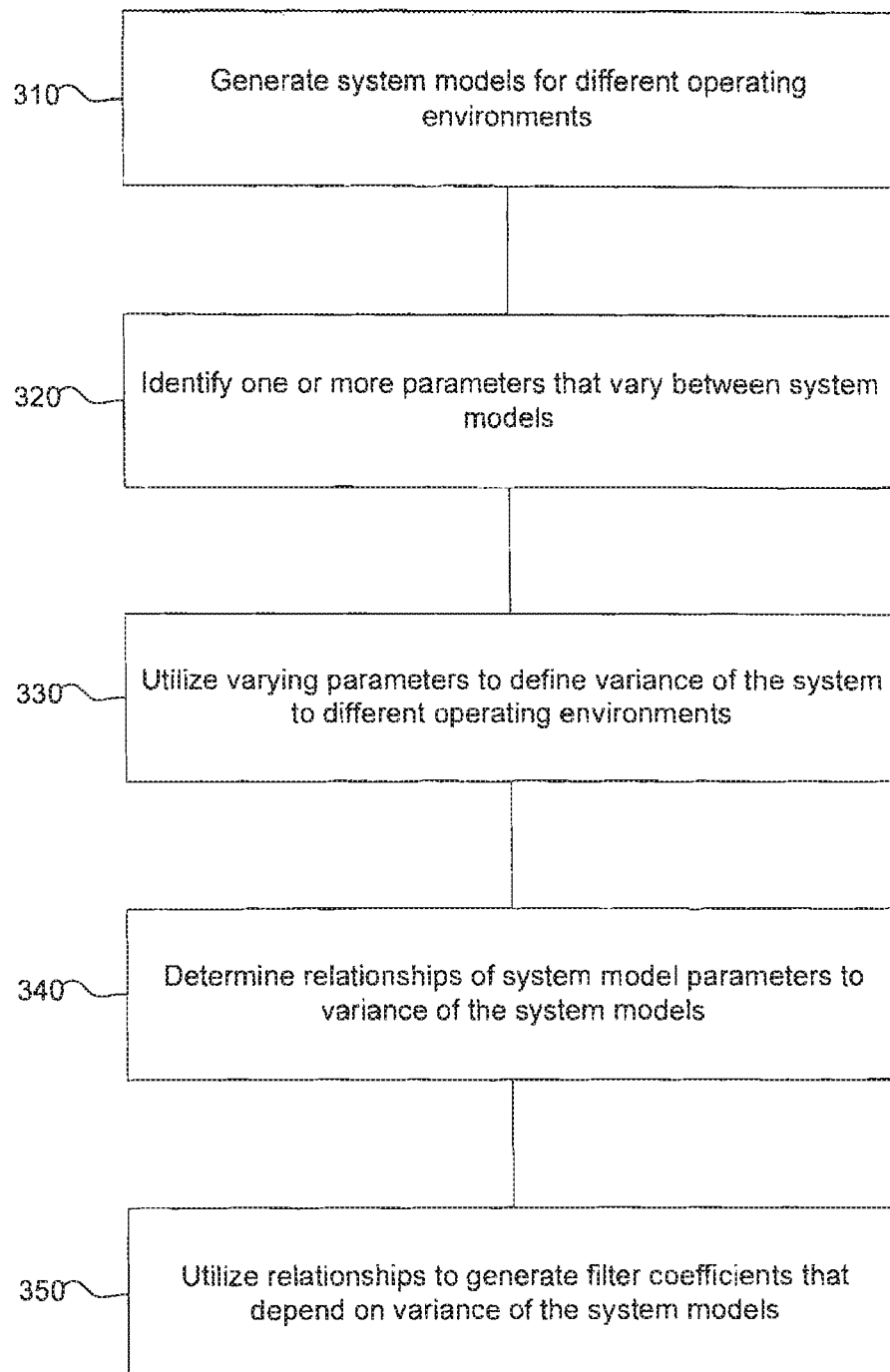
FIG. 7 is a process flow sheet.

In order to implement the system of FIG. 6, it will be appreciated that a filter must be generated where the filter coefficients are dependent upon a latent variable that is associated with variable operating conditions/environment of the implantable hearing instrument. FIGS. 7-10 provide a broad overview of how dependency of the adaptive filter on varying operating conditions is established. FIG. 7 illustrates an overall process 300 for generating a filter having coefficients that depend on a latent variable. Initially, the process requires two or more system models be generated for different operating environments. For instance, system models may be generated based on posture while a patient is looking to the left, straight ahead, to the right and/or tilted. The system models may be generated according to any appropriate methodology. Once such system models are generated 310, parameters of each of the system models may be identified 320, Specifically, parameters that vary between the different system models and hence different operating environments may be identified 320.

Figure 8:
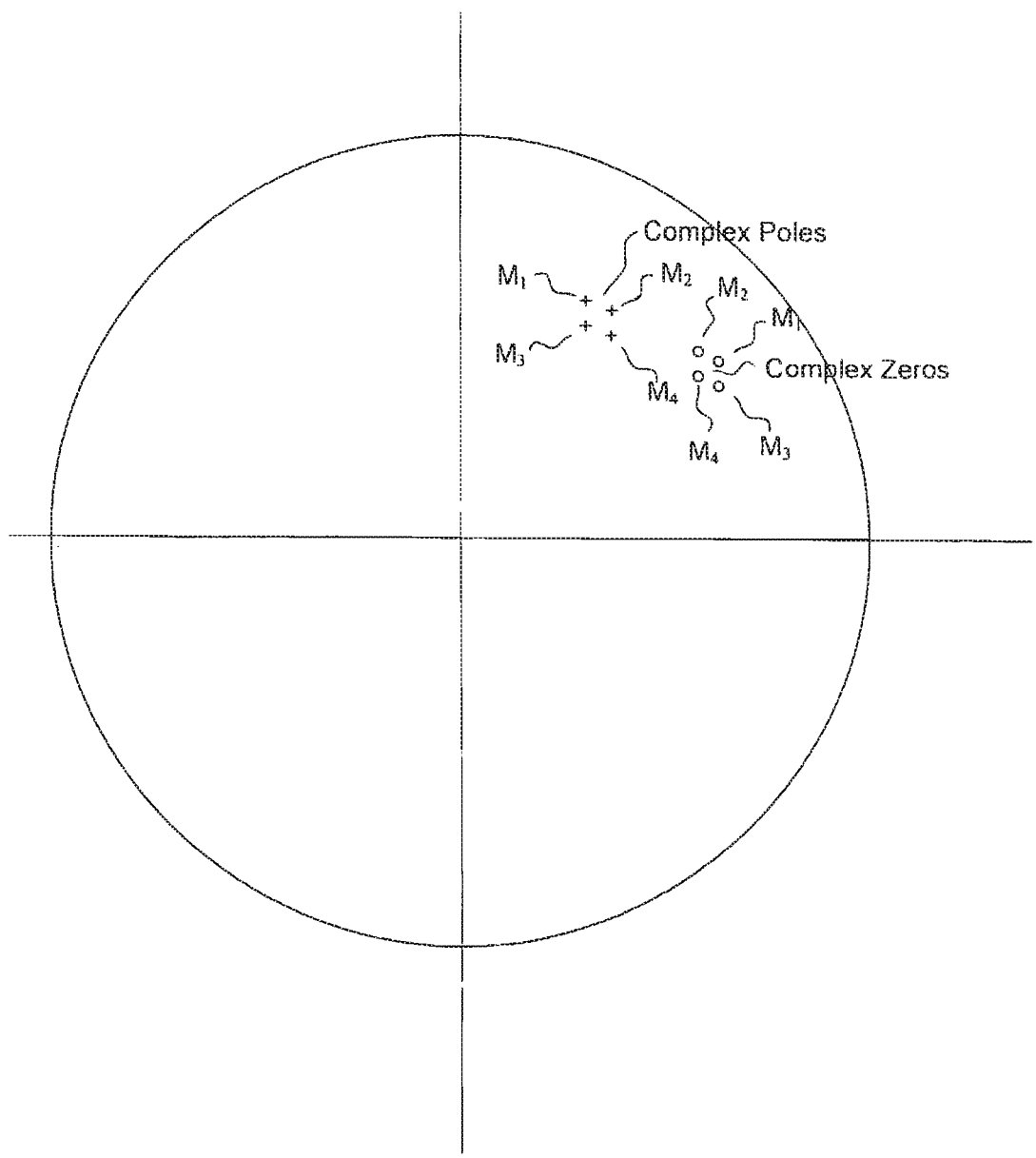
FIG. 8 illustrates a plot of operating parameters in the unit circle in the "z" dimension.
Figure 9:
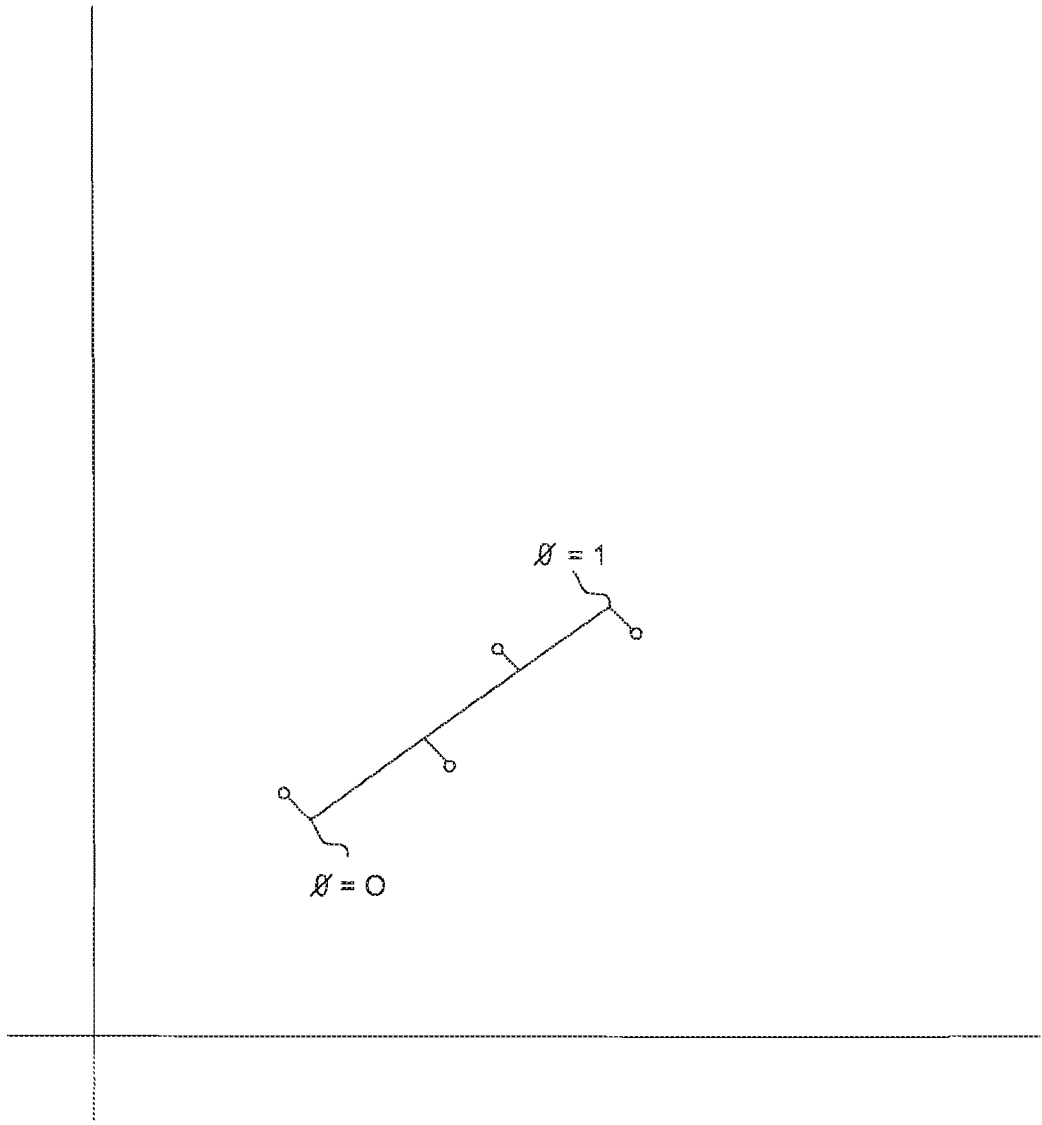
FIG. 9 illustrates fitting a line to a first set of operating parameters to define a range of a latent variable.

For instance, each system model may include multiple dimensions that form the parameters of the models. Such dimensions may include, without limitation, gain, a real pole, a real zero, as well as complex poles and zeros. Further, it will be appreciated that complex poles and zeros may include a radius as well as an angular dimension. In any case, a set of these parameters that vary between different models (i.e., and different operating environments) may be identified. For instance, it may be determined that the complex radius and complex angle and gain (i.e., three parameters) of each system model show variation for different operating conditions. For instance, FIG. 8 illustrates a plot of a unit circle in a "z" dimension. As shown, the complex zeros and complex poles for four system models $M_1$-$M_4$ are projected onto the plot. As can be seen, there is some variance between the parameters of the different system models. However, it will be appreciated that other representations of the filter parameters may be selected. What is important is that the parameters selected vary between the system models and this variance is caused by change in the operating condition of the implantable hearing instrument.

Once the variable parameters are identified 320, they may be projected 330 onto a subspace. In the present arrangement, where multiple parameters are selected, this may entail performing a principle component analysis on the selected parameters in order to reduce their dimensionality. Specifically in the present embodiment, principle component analysis is performed to reduce dimensionality to a lower dimension (e.g., a single dimension) such that a subspace (e.g., a line) may be fit to the resulting data points. See FIG. 9. In one arrangement, the subspace is chosen to have the same dimensionality of the space spanned by the latent variable. Accordingly, this data may represent operating environment variance or latent variable for the system. For instance, in the present arrangement where four system models are based on four different postures of the user, the variance may represent a posture value.

Figure 10:
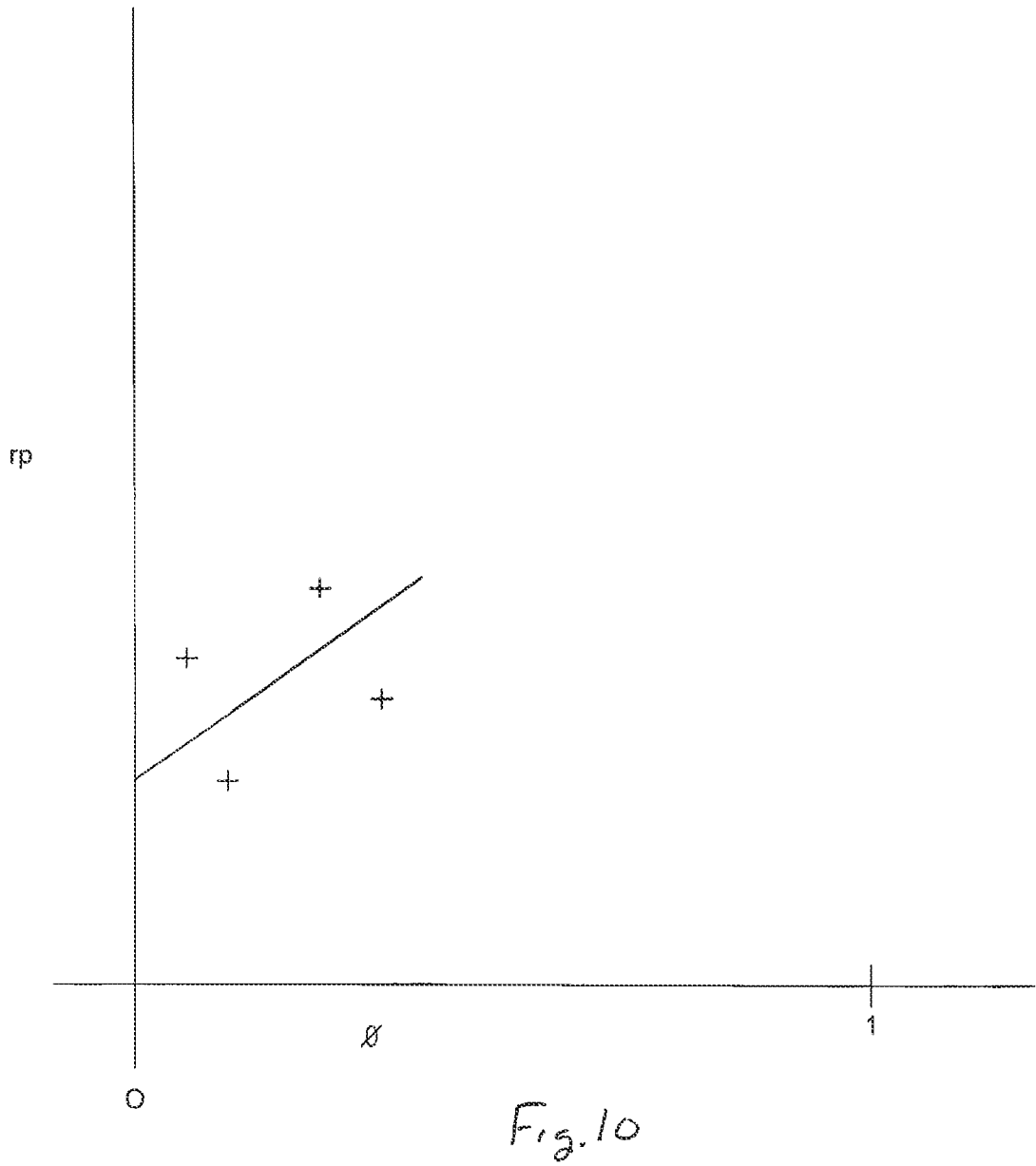
FIG. 10 illustrates a linear regression analysis of system parameters to the latent variable.

Further, the plot may define the range of the latent variable Θ. That is, a subspace, which in this case is a line, is fit to the data and may define the limits of the latent variable. For instance, a first end of the line may be defined as zero, and the second end of the line may be defined as one. At this point, a latent variable value for each system model may be identified. Further, the relationship of the remaining parameters of each of the system models may be determined relative to the latent variables of the system models. For instance, as shown in FIG. 10, a linear regression analysis of all the real poles of the four system models to the latent variable may be projected. In this regard, the relationship of each of the parameters (i.e., real poles, real zeros, etc.) relative to the latent variable may be determined. For instance, a slope of the resulting linear regression may be utilized as a sensitivity for each parameter. Accordingly, this relationship between the parameters and the latent variable are determined, this information may be utilized to generate a coefficient vector, where the coefficient vector may be implemented with the cancellation filters 90, 92 of the system of FIG. 6. As will be appreciated, the coefficient vector will be dependent upon the latent variable. Accordingly, by adjusting a single value (the latent variable), all of the coefficients may be adjusted. Generation of such a coefficient vector is more fully discussed in co-pending U.S. application Ser. No. 11/565,014, entitled "Adaptive Cancellation System for Implantable Hearing Instruments," having a filing date of Nov. 30, 2006, the contents of which are incorporated by reference herein. It will be appreciated that, as the linear regression of the filter is often an ill-posed problem (i.e., that is not having one single solution) that various regularizing factors may also be used. Such regularizing factors may include, but are not limited to, the distance of the postures from the desired dimensionality and/or the compactness of clusters of poles and/or zeros.

While the use of the latent variable arrangement may allow for adapting to changing environmental conditions, the use of such a system may result in the introduction of electrical noise in the implantable hearing system. As will be appreciated, all electrical components (e.g., the microphone 10 and motion sensor 70) generate electrical noise during their operation. Further, as amplification/gain is generally applied to the motion sensor output Acc in order to match the output response Mic of the microphone 10, the electrical noise of motion sensor 70 is likewise amplified. For instance, if 6 dB of gain is applied to the motion sensor output response Acc, the 6 dB of gain is also applied to the electrical noise of the motion sensor 70. Unfortunately, the variance of the electrical noise of the motion sensor is additive to the variance of the electrical noise of the microphone 10. That is, the electrical noise of these components do not cancel out. Accordingly, in some instances, the use of the motion sensor output may add noise to the system. Specifically, when little biological noise is present, the use of a motion sensor output response to cancel transducer feedback may increase the total noise of the implanted hearing system. If the noise floor is high enough, the electrical noise of the system, may encroach on soft speech sounds, reducing speech intelligibility of a user of the implanted hearing system.

Figure 11:
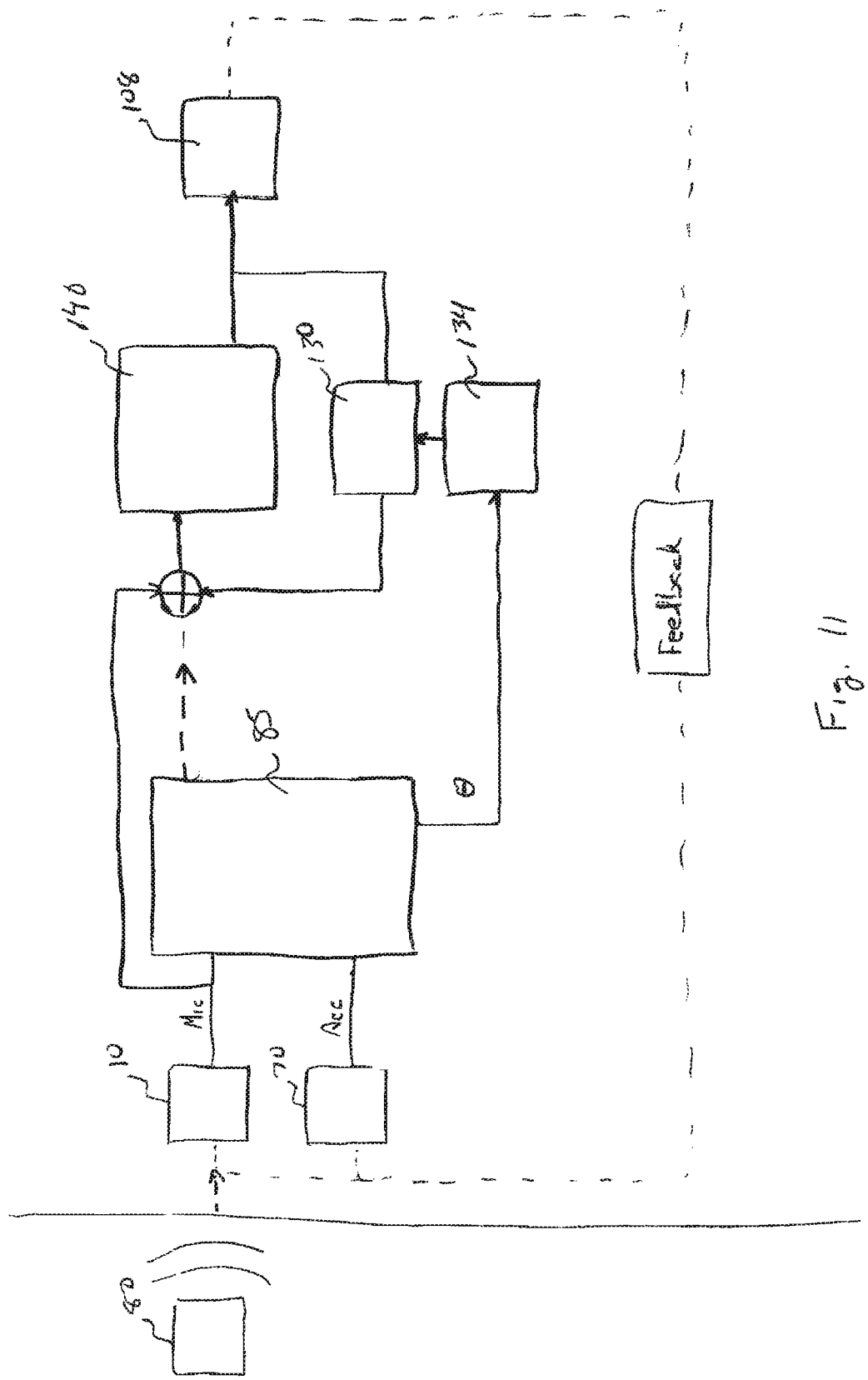
FIG. 11 is a schematic illustration of one embodiment of an implanted microphone system that utilizes an observer to detect current operating conditions for cancellation purposes.

FIG. 11 illustrates a system that reduces the introduction of electrical noise into an implantable hearing system while allowing the system to adjust to changing environments. In this arrangement, an observer 85 based on the output signals of the microphone 10 and motion sensor 70 (e.g., a first cancellation system) are utilized to identify a current operating condition of the implantable hearing system. In control theory, a device which determines the state of a system is called an observer. As discussed above, a latent variable (which can be considered a state vector) can be effectively determined by adaptively adjusting presumed values of vector components (and the corresponding digital filter coefficients) until maximum cancellation between a microphone and the filtered output of a motion detector are determined. Thus, such an arrangement can be used as an observer for determining a current operating environment/condition (e.g., posture) of an implanted hearing system patient. In this regard, the observer 85 of the present embodiment may be formed using the latent variable cancellation system 84 discussed in relation to FIG. 6. Other systems may be utilized to form an observer as well.

Once the observer 85 determines a current operating condition/state, a second cancellation system then utilizes information regarding the current operating condition to adjust a filter that is utilized to filter the digital output of the implantable hearing instrument and combine the resulting filtered output with the microphone output signal to reduce feedback That is, once a current operating condition (e.g., posture) is determined, a second set of digital filter coefficients can be determined for the current operating conditions. Though the current operating condition may be associated with various different operating environments or conditions, the following discussion is directed to an embodiment where the operating condition of interest is related to posture. Such reference to posture is by way of example and is no way a limitation.

The second set of filter coefficients are used to set a second filter 130 (e.g., digital filter) so as to properly shape the output of the hearing instrument to cancel out the response of the microphone to feedback from the operation of an implanted auditory stimulation device (e.g., transducer 108). Stated otherwise, the implanted hearing system is operative to utilize a first cancellation system (i.e., first control loop) to adjust a second cancellation system (i.e., second control loop) to control feedback, while minimizing electronic noise. In this regard, the first control loop utilizes a motion sensor 70 and a filter to match the output signal Acc of the motion sensor 70 to the output signal of the microphone assembly 10. In the present embodiment, the operation of the first control loop is substantially similar to the system discussed in relation to FIG. 6 where the output signal of a motion sensor 70 is scaled and/or frequency shifted (i.e., filtered) and removed from the output signal of the microphone 10 in order to minimize a residual energy in a resulting net signal. In contrast, the second control loop is an internal feedback loop where the digital output of the signal processor 140 of the hearing instrument is inserted back to the input of the signal processor 140 via a digital filter 130.

Generally, the second control loop eliminates feedback from the input to the processor 140 by providing an additional feedback loop of the same magnitude but opposite phase through a second path. That is, in addition to feedback through a tissue feedback path 78, the digital output of the signal processor 140 is inserted back to the input via a digital filter 130 (i.e., through the internal control loop). A number of different control structures for adjusting the parameters of this digital filter are known in the signal processing arts. The thrust of all of these control structures is to make the internal loop (i.e., the digital filter 130) act as a good model of the external feedback loop 78. Subtracting the filtered internal loop feedback (i.e., the model) from the microphone output signal (which contains a desired signal and feedback) results in the desired signals being passed on for further processing substantially free of feedback. The advantages of this type of internal loop are 1) Simplicity—no additional sensors are used and 2) low noise as the digital signal output signal is never converted into an analog signal prior to being filtered and reinserted into the signal processor 130. The only noise introduced into the system is from the electrical noise of the microphone and quantization noise.

In order to allow for adjusting the digital filter 130 an operating condition specific vector θ (e.g. posture vector) determined by the observer 85 is provided to a filter coefficient generator 134 for use in generating filter coefficients for the digital filter 130. As will be appreciated, the observer 85 may be a filter system of low complexity such that it may respond rapidly to changes in operating conditions. Likewise, this allows the filter coefficients to be rapidly generated the filter coefficient generator 134 for use with the digital filter 130. Such a system, unlike systems which only use the output of the hearing instrument, largely ignores correlation within the signal, so that highly self-similar signals, such as music and alarm tones, are not cancelled.

As discussed above in relation to FIGS. 7-10, during the fitting process for a subspace projection-type cancellation on which the observer is based, a technician measures the microphone and the motion sensor outputs and determines the transfer function between the two when excited by a known signal, such as a maximum length sequence (MLS) signal. This transfer function is then used to generate a model, here using a relatively low order digital (IIR) filter. The coefficients for the model are developed in one of several ways. For instance, a linear subspace projection of the most relevant 1, 2 or 3 posture dimensions is sufficient in most cases. The posture parameters are mapped from the maximum range of each pole and zero as well as the gain. An additional safety factor may be multiplied in to allow for postures beyond the range that were measured to be properly cancelled.

In the second loop, the transfer function is determined not from the motion sensor 70 to the microphone 10, but from the output (MLS) of the processor 130 of the hearing instrument to the microphone 10. Again, the transfer functions for each posture can be simply linearly mapped onto the 1, 2, or 3 posture dimensions of most relevance. In this case, however, the posture parameters used are not developed from the range of the poles, zeros, and gain of the second filter, but are the same posture vectors determined from the first (observer) model. A linear map is used to go from the posture parameters to the filter coefficients for the second filter (higher order maps may be used, but are probably unnecessary).

Because the very few (1, 2, or 3 dimensions) posture vector elements are determined by the observer 85, and then mapped into the filter coefficients appropriate for canceling feedback at that posture, the digital filter 130 may have a large number of taps. It may be FIR or IIR, or a combination. Time delays may be added in. No complicated control system is needed, since all of the coefficients of the filter (IIR, FIR and/or time delay) are determined from the posture vector with a very low dimension. Thus, the generator 134 can easily and quickly adjust the coefficients for an FIR filter with say 32 coefficients.

Such a system has the feedback substantially or completely removed by the second control loop, but does not have the biological noises altered in anyway, since they do not originate from the feedback loop. The biological noise level may therefore be louder than in a normal subject. In contrast, the internal cancellation performed in the observer 85 to determine the current operating condition has most of the biological noise removed, and hence the biological noise level is quieter than normal. If desired, the observer cancelled output (e.g., net signal), may be combined with the net signal generated by combining the filtered digital output with the microphone signal to yield a more natural combination. This may come at the cost of some increase in circuit/electrical noise from the motion sensor 70. However, combining the low frequency component of the observer output signal with the high frequency output of the second filter cancellation yields a good compromise, since most of the biological noise occurs at low frequencies and most of the objectionable noise power from the motion sensor 70 occurs at high frequencies.

Those skilled in the art will appreciate variations of the above-described embodiments that fall within the scope of the invention. For instance, sub-band processing may be utilized to implement filtering of different outputs. As a result, the invention is not limited to the specific examples and illustrations discussed above, but only by the following claims and their equivalents.

The invention claimed is:

1. A method for use in an implantable hearing instrument having an implantable microphone, comprising:
    identifying, based on one or more variables that change with respect to changes in an operating environment of the implantable hearing instrument, a current operating condition of an implantable hearing instrument, wherein said identified current operating condition is automatically identified based on one or more variables that change with respect to changes in posture of a wearer of the implantable hearing instrument, said variables being related to a predetermined plurality of different postures of a wearer of the implantable hearing instrument;
    establishing filter settings for a cancellation filter based on said identified current operating condition; and
    utilizing said cancellation filter to cancel signals from a microphone output response of the implantable microphone.

2. The method of claim 1, wherein using said cancellation filter to cancel signals comprises:
    filtering a digital output signal of the hearing system to generate a filtered output; and
    combining the filtered output with the microphone output response to generate a net signal.

3. The method of claim 1, wherein identifying a current operating condition comprises:
    combining a microphone output response of an implantable microphone with a motion sensor output response of a motion sensor, wherein the motion sensor output response is filtered by a filter having a transfer function associated with responses of the motion sensor and implantable microphone, and wherein combining the responses produces a first net signal;
    adjusting the filter having the transfer function to reduce a residual energy of said first net signal; and
    upon reducing the residual energy to a desired degree, determining said identified operating condition based at least in part on settings of said filter.

4. The method of claim 1, wherein the variables change with respect to changes in a posture of the wearer of the implantable hearing instrument, and wherein the action of identifying said current operating condition includes comparing the variables to data based on a predetermined plurality of different postures of a wearer of the implantable hearing instrument.

5. The method of claim 4, further comprising:
    upon identifying the current operating condition, selecting filter coefficients for said cancellation filter based on said current posture.

6. The method of claim 5, wherein selecting filter coefficients comprises interpolating said coefficients from at least two posture related models associated with said cancellation filter.

7. The method of claim 1, wherein identifying the current operating condition comprises:
    utilizing an observer to determine the operating condition, wherein the observer generates an output indicative of said operating condition.

8. A method for use in an implantable hearing instrument having an implantable microphone, comprising:
    combining a microphone output response of an implantable microphone with a motion sensor output response of a motion sensor, wherein the motion sensor output response is filtered by a first filter prior to combining the response, and wherein combining the responses produces a first net signal;
    adjusting the first filter to reduce a residual energy of said first net signal to a desired degree by adjusting an operating condition dependent variable that is common to multiple coefficients of said first filter based on input indicative of a variation in posture of a recipient of the implantable hearing instrument; and
    upon reducing the residual energy to the desired degree, utilizing settings of said first filter to establish filter settings of a second filter; and
    utilizing said second filter to cancel signals from a microphone output response of the implantable microphone.

9. The method of claim 8, wherein using said second filter to cancel signals comprises:
using said second filter to filter an output drive signal of the hearing system to generate filtered output; and
combining the filtered output with the microphone output response to generate a second net signal.

10. The method of claim 9, further comprising:
utilizing said second net signal to generate an output drive signal for an auditory stimulator of said implantable hearing system.

11. The method of claim 8, wherein adjusting the first filter comprises:
adjusting an operating condition dependent variable that is common to multiple coefficients of said first filter based on input indicative of a variation in posture of a recipient of the implantable hearing instrument.

12. The method of claim 8, wherein a first transfer function of the first filter is determined from a relationship between response of the motion sensor and the implanted microphone and a second transfer function of the second filter is determined from a relationship between an output drive signal of the hearing instrument and a response of the implanted microphone.

13. The method of claim 2, wherein said net signal is utilized by the hearing instrument to generate a subsequent output signal, the method further comprising:
processing the net signal with a signal processor to generate the subsequent output signal; and
directing the output signal to a transducer that interfaces with an organ of a recipient of the implantable hearing instrument to drive the transducer.

14. The method of claim 8, wherein:
the action of establishing filter settings of the second filter is performed without regard to the combined microphone output response with the motion sensor output response.

15. The method of claim 8, wherein:
the action of establishing filter settings of the second filter is performed based solely on the settings of said first filter.

16. A method of using an implantable prosthesis having an implantable vibration sensor, comprising:
receiving input indicative of a change in an operating environment of the implantable prosthesis, wherein the change in the operating environment changes a vibration communicative property of skin overlying the vibration sensor;
processing first signals based on the received input; and
cancelling vibration sensor output response signals of the implantable vibration sensor utilizing the processed first signals.

17. The method of claim 16, wherein:
the action of processing the first signals entails processing the first signals utilizing a filter; and
the method further comprises varying a filter coefficient of the filter based on the received input.

18. The method of claim 16, further comprising:
processing second signals to obtain transducer control signals, the second signals resulting at least in part from the cancellation of the microphone output response signals; and
directing the transducer control signals to a transducer that interfaces with an organ of a recipient of the implantable prosthesis to drive the transducer, wherein
the transducer control signals are filtered to obtain the processed first signals.

19. The method of claim 16, further comprising:
obtaining transducer control signals configured to drive a transducer that interfaces with an organ of a recipient of the implantable, wherein the transducer control signals correspond at least in part to the first signals.

20. The method of claim 16, further comprising:
inputting the input indicative of the change in the operating environment into an observer; and
processing the first signals based on output of the observer.

21. The method of claim 16, wherein:
the action of processing the first signals based on output of the observer is based solely on the output of the observer.

22. The method of claim 21, wherein:
the input into the observer consists of input from a microphone and input from a motion sensor.

* * * * *